United States Patent
Hsieh

(10) Patent No.: US 6,913,890 B2
(45) Date of Patent: Jul. 5, 2005

(54) PROCESS FOR PREPARING ALBUMIN PROTEIN CONJUGATED OLIGONUCLEOTIDE PROBES

(75) Inventor: Huangpin Ben Hsieh, Mountain View, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 10 days.

(21) Appl. No.: 10/323,385

(22) Filed: Dec. 18, 2002

(65) Prior Publication Data

US 2004/0121426 A1 Jun. 24, 2004

(51) Int. Cl.[7] ............................ C12Q 1/68; C12P 19/34; G01N 33/00; C07H 21/02
(52) U.S. Cl. ............................ 435/6; 435/91.1; 436/94; 536/23.1; 536/24.3
(58) Field of Search ............................ 435/6, 7.1, 91.1, 435/183; 436/94; 536/23.1, 24.3, 25.3; 530/300, 350

(56) References Cited

U.S. PATENT DOCUMENTS 5,939,383 A * 8/1999 Remacle et al. ................ 514/9

| | | | |
|---|---|---|---|
| 2002/0051788 A1 | 5/2002 | Pozsgay | |
| 2002/0068818 A1 | 6/2002 | Pozsgay | |
| 2002/0146504 A1 | 10/2002 | Schwartz | |
| 2004/0038331 A1 * | 2/2004 | Reddy et al. | 435/68.1 |

OTHER PUBLICATIONS

Bidaine et al., The phototrityl group photocrosslinking of oligonucleotides to BSA. Bioorganic & Medicinal Chemistry Letters, 6, 1167–1170, 1996.*

Bonfils et al, "Drug Targeting: Synthesis and Endocytosis of . . . ", Nucleic Acids Research, vol. 20, No. 17, 1992, pp 4621–4629.

* cited by examiner

*Primary Examiner*—Kenneth R. Horlick
*Assistant Examiner*—Frank W. Lu
(74) *Attorney, Agent, or Firm*—Fay, Sharpe, Fagan, Minnich & McKee, LLP

(57) ABSTRACT

A technique for forming conjugates of proteins and oligonucleotides is disclosed in which conjugation is performed while the oligonucleotide is attached to support media such as glass beads. The conjugated product may then be readily removed from the support media. Also disclosed are the conjugated products formed by this technique. The present invention is particularly directed to conjugates of albumin proteins and specifically to bovine serum albumin (BSA).

13 Claims, No Drawings

SEQUENCE LISTING

<160> NUMBER OF SEQ ID NOS: 1

<210> SEQ ID NO 1
<211> LENGTH: 17
<212> TYPE: DNA
<213> ORGANISM: Unknown
<220> FEATURE:
<223> OTHER INFORMATION: sequence to a PCR amplified product generated
      from a control DNA and a pair of primers in a primer mixture
<220> FEATURE:
<221> NAME/KEY: 5'clip

```
-continued

<222> LOCATION: (1)..(17)
<223> OTHER INFORMATION: sequences to a PCR amplified product generated
      from a control DNA and a pair of primers in a primer mixture

<400> SEQUENCE: 1
cagacttacg cagctcc                                                    17
```

PROCESS FOR PREPARING ALBUMIN PROTEIN CONJUGATED OLIGONUCLEOTIDE PROBES

FIELD OF THE INVENTION

The present invention relates to techniques for preparing conjugates of protein and oligonucleotides, and the conjugates formed by these techniques. More specifically, the invention is directed to the preparation of conjugates of albumin protein and oligonucleotides, and the resulting conjugates thereof.

BACKGROUND OF THE INVENTION

Oligonucleotides and their analogs are widely used as research reagents. They are useful in understanding the preparation and function of many biological molecules. For example, the use of oligonucleotides and their analogs as primers in polymerase chain reactions (PCR) has given rise to an expanding commercial industry. PCR has become of significant importance in commercial and research laboratories, and applications of PCR have multiplied. For example, PCR technology is now utilized in the fields of forensics, paleontology, evolutionary studies and genetics. Commercialization has led to the development of kits which assist non-molecular biology-trained personnel in applying PCR. Oligonucleotides and their analogs, both natural and synthetic, are employed as primers in such PCR technology.

Oligonucleotides and their analogs can be synthesized to have customized properties that can be tailored for particular uses. Thus a number of chemical modifications have been introduced into oligomers to increase their usefulness in diagnostics, as research reagents and as therapeutic agents. Such modifications include those designed to increase binding to a target strand, to assist in identification of the oligonucleotide or an oligonucleotide-target complex, to increase cell penetration, to stabilize against nucleases and other enzymes that degrade or interfere with the structure or activity of the oligonucleotides and their analogs, to provide a mode of disruption (terminating event) once sequence-specifically bound to a target, and to improve the pharmacokinetic properties of the oligonucleotide.

Short oligonucleotide probes used in molecular diagnostic arrays often contain albumin proteins and more specifically, covalently bound proteins such as bovine serum albumin (BSA) to enhance their binding to substrates such as nylon membranes or glass slides. Albumin generally refers to serum albumin. Albumin describes a protein or group of proteins typically found in the mammalian circulatory system. Generally, albumins are characterized by their solubility in water.

Manufacturing probes of conjugated oligonucleotides and BSA traditionally involves attaching BSA to oligonucleotides after the oligonucleotides have been synthesized and cleaved off glass beads employed in their synthesis. However, separation of excess (unconjugated) BSA which has similar molecular weight (66 kDa) to the conjugated oligonucleotide-BSA (~72 kDa) products frequently involves high performance liquid chromatography (HPLC) purification. This process is expensive and time-consuming, resulting in a bottleneck for the probe manufacturing process. Accordingly, there is a need for an improved method of preparing conjugates of oligonucleotides and protein, more preferably albumin protein, and specifically BSA.

Prior artisans have described various conjugates and their preparation. Several prior investigations have involved conjugates of oligonucleotides and certain types of proteins. For example, in WO220544A1 entitled "Process for Preparing Peptide Derivatized Oligomeric Compounds" Manoharan et al. describe a process of using equimolar amounts of oligomeric compounds and peptide reagents in order to increase overall synthesis efficiency. This method is useful for preparing large scale amounts of peptide linked oligomeric compounds.

The process described by Manoharan et al. is not directly applicable to preparing conjugates of BSA as the stochiometry is different. In fact, the process described by Manoharan et al. has nothing to do with an enhanced synthesis method that could eliminate one or more downstream purification operations.

U.S. Pat. No. 6,210,908 entitled, "Activated Peptides and Conjugates" to Annunziato et al., describes a process that can be used to fabricate peptide conjugates for use as antigen, specific to some immunoreactive antibody. The process can enhance the yield of peptides with terminal amine-linked conjugates and decreases the reactivity of internal amine groups such that the peptide conjugate is more effective. However, this process is not particularly relevant to addressing the foregoing noted problems.

U.S. Pat. No. 5,977,299 entitled "Activated Peptides and Conjugates" describes the same process as the previously noted U.S. Pat. No. 6,210,908. And so, the '299 patent is not particularly relevant.

U.S. Pat. No. 5,767,238 entitled "Inverse Solid Phase Synthesis" is directed to a process for solution phase (homogeneous) synthesis for large chemical libraries. A large soluble polymeric group is used as support for oligonucleotide or peptide synthesis and is also subsequently used to separate products from unreacted reactants by the large size of the polymer-associated products. This process is described as improving the yield and allowing for easy purification.

It is also known to conjugate oligonucleotides with high molecular weight polyethylene glycols (PEGs), such as described in "Synthesis by High-Efficiency Liquid-Phase (HELP) Method of Oligonucleotides Conjugated with High-Molecular Weight Polyethylene Glycols (PEGs)." G. M. Bonora et at., Biological Procedures Online, vol. 1, No. 1, May 14, 1998, However, these techniques are not applicable to the objective of conjugating an oligonucleotide to a protein, and more desirably, to an albumin protein such as BSA.

Although satisfactory in certain respects, there still remains a need for a relatively simple and economical technique for preparing conjugates of protein, and more particularly an albumin protein such as BSA, and oligonucleotides that are particularly adapted for diagnostic assays.

SUMMARY OF THE INVENTION

In a first aspect, the present invention provides a process for producing an oligonucleotide-protein conjugate. The process comprises a step of providing a support media adapted for retaining an oligonucleotide. The process further includes a step of attaching an oligonucleotide to the support media. The process further includes a step of providing an albumin protein for subsequent coupling to the oligonucleotide. The process additionally includes a step of coupling the protein to the oligonucleotide while the oligonucleotide is attached to the support media to form the oligonucleotide-protein conjugate. The invention also includes the conjugates produced by this process.

In another aspect, the present invention provides a process for preparing protein conjugated oligonucleotides by providing a support media adapted for coupling an oligonucleotide. The process further includes a step of providing a first solution including the oligonucleotide. The process further includes a step of passing the first solution through the support media to thereby couple the oligonucleotide to the support media. The process further includes a step of providing a second solution including an albumin protein adapted to form a conjugate with the oligonucleotide. The process further includes a step of passing the second solution through the support media after the passing of the first solution through the support media, thereby conjugating the protein with the oligonucleotide while the oligonucleotide is coupled to the support media to form the protein conjugated oligonucleotide. The process further includes a step of removing the protein conjugated oligonucleotides from the support media. The invention also includes the conjugates produced by this process.

In yet another aspect, the present invention provides a process for producing a conjugate of BSA and oligonucleotide. The process includes a step of providing a support media adapted for coupling an oligonucleotide. The process further includes a step of passing an oligonucleotide through the support media and thereby coupling at least a portion of the oligonucleotide on the support media. The process further includes a step of, after passing through and coupling the oligonucleotide to the support media, passing an effective amount of bovine serum albumin (BSA) through the support media and thereby forming the conjugate of BSA and oligonucleotide that is coupled to the support media. The process additionally includes a step of decoupling the conjugate of BSA and oligonucleotide from the support media. The invention additionally includes the conjugates produced according to this process.

In still another aspect, the present invention provides a conjugate of an oligonucleotide and BSA wherein the ratio of oligonucleotide to BSA ranges from about 5 to about 50.

DESCRIPTION OF THE PREFERRED EMBODIMENTS

The present invention provides a new process for producing conjugates of (i) oligonucleotides and (ii) protein in which the protein is preferably albumin protein and most preferably, BSA. The resulting conjugates may serve as oligonucleotide probes that are particularly well-suited for DNA array applications.

Opposite to the common practice in which conjugation is performed off-column, the present invention provides a unique technique in which conjugation is performed while the oligonucleotide is still retained on a support in the column. That is, the coupling of oligonucleotides with a protein, which is preferably an albumin protein and most preferably BSA, is performed while the oligonucleotide is still attached to a support in the synthesis column. More specifically, the present invention provides a process in which coupling between oligonucleotides and BSA is performed while the oligonucleotide is attached to a support media such as controlled pore size glass beads typically used in synthesis. The advantage of this strategy is that purification of the conjugate product can be achieved by simply flushing the column with solvent when the conjugation reaction is complete. All, or substantially all, of the unbound BSA and undesired reactants are flushed away and the conjugated products are retained in the column and harvested with a simple reagent treatment. This new process has been successfully demonstrated. The elimination of the requirement for HPLC purification saves significant time and cost.

Coupling a protein such as BSA to oligonucleotides while the oligonucleotides are still attached to a support such as glass beads is an alternative and beneficial conjugate manufacturing process. Unconjugated BSA and other reactants are flushed away before the probes are cleaved off the support and harvested. These probes can then be used directly for array printing or other purposes without HPLC purification. Although free oligonucleotides may be present in the product mixture, the ratio is small. If necessary, a simple Sephadex G25 column can be used to separate the free oligonucleotides from conjugated products. Another advantage of the present invention is the desirable higher conjugation ratio of oligonucleotide to BSA achievable with this process as compared to conventional conjugation strategies.

Specifically, the present invention provides a new process in manufacturing BSA coupled oligonucleotide probes for DNA arrays. In a typical diagnostic DNA array manufacturing process, large quantities of oligonucleotides are routinely synthesized with a DNA synthesizer, cleaved off the solid support, and then conjugated with BSA to enhance their attachment to substrate. Uncoupled BSA used in the reaction needs to be separated from the products, which often requires HPLC purification. As previously noted, this extra purification step is time-consuming and significantly increases the cost of probe manufacturing.

In addition, the present invention provides a novel technique for conjugating BSA to the oligonucleotides while the oligonucleotides are still bound to the support media such as controlled-pore glass beads contained in the synthesis column. The coupling of oligonucleotides with a peptide that contains a free carboxyl group, a blocked N-terminus and no reactive side chains has been demonstrated. However, the process of conjugating a larger protein such as an albumin protein and specifically for instance BSA to an oligonucleotide represents significantly more challenges and has not yet been evaluated before.

The present invention may also be applicable to "bio-printing" of DNA arrays. The present invention may also be of interest to parties concerned with cost-saving and print-ready oligonucleotide manufacturing processes, as raw biomaterial constitutes a large portion of the manufacturing cost. The present invention is believed to provide a significant advance in this area of technology.

A significant aspect of the present invention is conjugating protein onto oligonucleotides still attached to the synthesis column. In application, an integrated oligonucleotide probe is manufactured with on-column protein conjugation. Also, the improved conjugation ratio of oligonucleotide to BSA is a feature as it reduces the amount of oligonucleotide probes (thus array feature volume) needed to achieve the same signal intensity.

As used herein, the term "oligonucleotide" includes oligomers or polymers containing two or more nucleotide subunits. Generally, the number of nucleotide units may range from about 2 to 100, and preferably from about 2 to 30 or 50 to 80. In the context of the present invention, the term "oligonucleotide" refers to a plurality of naturally-occurring or non-naturally-occurring nucleotides joined together in a specific sequence. Any synthetic oligonucleotides can be used. They can be any length, modified or unmodified at their 3'-end. Oligonucleotides according to the invention preferably have a ribofuranose moiety attached to a nucleobase through a glycosyl bond.

Although the present invention encompasses conjugating nearly any type of oligonucleotide, several factors influence the choice of oligonucleotide. As an amino linker is attached to the 5'-end of the oligonucleotide after its synthesis, the 5'-end should be free after synthesis. For oligonucleotides that require other forms of modification at their 5'-end, these modifications need to be compatible with the addition of the amino linker. Other than this factor, most oligonucleotides can be synthesized and used.

Although the present invention is primarily concerned with conjugating an albumin protein such as BSA to oligonucleotides, the invention includes conjugating a wide array of proteins to oligonucleotides. Since the present conjugation takes place between protein's carboxyl group and amine groups on the amino linker, any agent that possesses a carboxyl group (—COOH) can be used for this conjugation. In addition, protein that has a free sulfhydryl (—SH) group can also be utilized in the noted conjugation. For certain applications, when the conjugate is used for stimulating immune response to generate antibodies, Keyhole Limpet Hemocyanin (KLH) is an example of a carrier protein that may be used. Due to the fact that all proteins possess one or more —COOH groups, nearly any protein can be conjugated using the present invention. Furthermore, in certain applications, it is contemplated that the present invention could also be used to conjugate proteins that are extremely unstable or which may degrade under basic ammonia hydroxide solution (used in the cleavage). The present invention techniques are contemplated to have a wide array of applications.

As noted, the present invention conjugation techniques and products preferably utilize one or more albumin proteins, and most preferably BSA. Albumins are characterized by a relatively low content of tryptophan and methionine and a high content of cystine and the amino acids aspartic and glutamic acids, lysine, and arginine. Albumins are known by their ability to reversibly bind to a wide array of compounds and ligands. BSA is a specific type of albumin protein and is the principal carrier of fatty acids that are otherwise insoluble in circulating plasma. Extensive description of various albumin proteins and specifically BSA is available in the literature. BSA is also widely commercially available. For example, BSA is available from Mallinckrodt Baker, Inc. of Phillipsburg, N.J. under the designation BSA H183 (C.A.S. 9048-46-8); and from Sigma-Aldrich of St. Louis, Mo. under the designation BSA A-7906.

The present invention methods also include preparation of oligomeric conjugates that include conjugate groups covalently bound to functional groups such as primary or secondary hydroxyl groups. Conjugate groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, phospholipids, biotin, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US/09196, filed Oct. 23, 1992; U.S. Pat. No. 5,578,718, issued Jul. 1, 1997; and U.S. Pat. No. 5,218,105. The entire disclosure of each is incorporated herein by reference.

As noted, the preferred methods for producing the noted conjugates utilize support media. A support media can be purchased from a commercial source with a linking moiety for attaching the nucleotide or alternatively, a support media can be modified with a desired linker. A preferred linking moiety is bifunctional and upon cleavage remains attached to the oligomeric compound such as for example 3'-thio-modifier C3S—S CPG (controlled pore glass). The linking moiety reversibly attaches the first added nucleotide or larger intermediate oligonucleotide to the support media which is then iteratively elongated to yield a final oligomeric compound, oligonucleotide or conjugate.

Conjugation between BSA and an oligonucleotide generally occurs by introducing an amino linker to the oligonucleotide and then conjugating the BSA to the linker. One example of an amino linker is a C-12 amino linker. Other linkers include, without limitation, a C-6 amino or any other numbers of carbons on the chain such as, for instance, 5'-Amino-Modifier C6, 5'-Amino-Modifier C5, and 5'-Amino-Modifier C3.

Support media can be selected to be insoluble or have variable solubility in different solvents to allow the growing oligomer or the oligomer-conjugate to be kept out of or in solution as desired. Traditional solid supports are insoluble and are routinely placed in a reaction vessel while reagents and solvents react or wash the growing chain until cleavage frees the final oligomer. More recent approaches have introduced soluble supports including soluble polymer supports to allow precipitating and dissolving the bound oligomer at desired points in the synthesis (Gravert et at., Chem. Rev., 1997, 97, 489–510, herein incorporated by reference.). Representative support media that are amenable to the methods of the present invention include without limitation: controlled pore glass (CPG); oxalyl-controlled pore glass (see, e.g., Alul, et al., Nucleic Acids Research 1991, 19, 1527); TENTAGEL Support, (see, e.g., Wright, et al., Tetrahedron Letters 1993, 34, 3373); or POROS, a copolymer of polystyrene/divinylbenzene available from Perceptive Biosystems. The use of a soluble support media, poly (ethylene glycol), with molecular weights between 5 and 20 kDa, for large-scale synthesis of phosphorothioate oligonucleotides is described in, Bonora et al., Organic Process Research & Development, 2000, 4, 225–231, herein incorporated by reference. Nearly any type of support media may be utilized in the methods of the present invention. Generally, a support media commonly used in the synthesis of oligonucleotides should be acceptable for the synthesis and cleavage of the resulting conjugate. If it is compatible with the conjugation conditions, then such media can be used.

After synthesis and conjugation with protein, the resulting oligomeric conjugate generally is cleaved from the solid support to obtain the free conjugate. In a preferred embodiment, cleavage of the final oligomeric conjugate following synthesis is accomplished using a solution of ammonium hydroxide ($NH_4OH$ (30%)) for 15 hours at 60° C., then filtered, and rinsed with ethanol/water (1/1, v/v). The combined solutions are preferably evaporated to dryness under vacuum. Other acceptable solutions include ammonium hydroxide/methylamine. Cleavage and de-protection reactions are faster with ammonium hydroxide/methylamine, but methylamine smells and also such solution can reduce the S=S bonds and so is not desired when an —SH group is involved in conjugation.

Once removed from the support media, the conjugate product may optionally be purified. It will be appreciated that although the present invention techniques eliminate the requirement of subjecting the conjugate product to one or more purification operations, such may still be employed. This determination is primarily dictated by the particular application and purity requirements for the conjugate product.

The purification of oligomeric conjugates may be performed by reversed phase high performance liquid chromatography (RP-HPLC) performed on a Waters Nova-Pak C18 column (3.9×300 mm) using a Waters HPLC system (600E System Controller, 996 Photodiode Array Detector, 717 Autosampler). For analysis, an acetonitrile (A)/0.1M triethylammonium acetate gradient is used: 5% to 35% A from 0 to 10 min, then 35% to 40% A from 10 to 20 min, then 40% to 95% A from 20 to 25 min, flow rate=10 mL/min/50% A from 8 to 9 min, 9 to 26 min at 50%, flow rate=1.0 mL/min, tR (DMT-off) 10–11 min, tR (DMT-on) 14–16 min. The DMT-on fractions are collected and are evaporated in vacuum, redissolved in water and the DMT group removed as described below. It will be appreciated that these techniques are representative in nature and that the present invention is not limited to such techniques. Other purification strategies include but are not limited to, reverse-phase cartridge (RP1) processes, and poly-acrylamide gel electrophoresis (PAGE) methods.

Oligomeric conjugates prepared by the methods of the present invention can be used in diagnostics, therapeutics and as research reagents and in kits. They can also be used in pharmaceutical compositions by including a suitable pharmaceutically acceptable diluent or carrier. They can further be used for treating organisms having certain diseases.

One difference between conjugates of oligonucleotides and BSA produced according to the present invention, as compared to conjugates produced in traditional methods is that BSA conjugated oligonucleotides produced by the present invention have a significantly higher conjugation ratio, meaning more oligonucleotides per BSA molecule.

More specifically, the conjugation ratio of oligonucleotide to BSA in conjugates produced according to the present invention may be higher (such as from about 5 to 50) than the conjugation ratio of similar conjugates produced by traditional techniques (such as from about 1 to 2.4). Based on the molecular weights of BSA (66 kDa) and a typical 20-mer oligonucleotide (600 Da), the BSA molecule is approximately 11-fold larger than the oligonucleotide. Although it is generally preferable to have a higher ratio of oligonucleotide per BSA to increase the signal intensity, the optimal range of conjugation ratio for DNA hybridization purposes is limited. By estimate, the conjugates of the present invention preferably exhibit a range of conjugation ratios of from about 1 to 50, more preferably 5 to 50, and most preferably between 5 and 20.

Furthermore, in a variation of the present invention, it is contemplated that the process described in U.S. Pat. No. 6,210,908, herein incorporated by reference, could be utilized as a technique to electively activate only terminal carboxyl groups.

In addition to eliminating a requirement of purifying a mixture of conjugate product and unbound BSA, such as by HPLC, other advantages stem from use of the present invention method as follows. The present invention techniques provide more freedom for conjugation conditions. Reactive sites of the synthesized oligonucleotides are protected during the conjugation by use of the present invention. In the conventional method where synthesized oligonucleotides are cleaved from a column before conjugation, the cleaving agents usually remove protective groups, thus making the subsequent conjugation reaction restricted due to the unprotected groups. Another advantage is that use of the present invention methods result in potentially higher yields, perhaps due to the constraints imposed on the oligonucleotide by its connection to the solid support.

EXAMPLES

An effective amount of an oligonucleotide was synthesized in a conventional manner and an amine was added to the 5'-hydroxyl of the oligonucleotide to serve as a linker between oligonucleotide and BSA. BSA and its C-terminal activating reagents were added to a synthesis cartridge and a coupling reaction allowed to occur over a period of time. The cartridge was then flushed and dried. A 30% ammonium hydroxide solution was added and the cartridge sealed. During the ammonia treatment, the oligonucleotide was cleaved from the support and the bases were fully deprotected. The ammonia solution was removed from the column and the conjugates are analyzed.

In order to improve the efficiency of coupling, the reaction was performed in organic solvent in which the activators are most soluble. The challenges of an oligonucleotide-BSA conjugation reaction include (1) the solubility of BSA in organic solution and its behavior, (2) multiple lysine amines exist on BSA which may compete with oligonucleotide amine for activated carboxyl groups, and (3) the possibility of denaturation of BSA in ammonia hydride solution.

Several aspects of the present invention address the above-mentioned challenges as follows.

For the solubility challenge (item (1) above), BSA was first dissolved in enough water before solubilized in organic conjugation buffer. Conjugation indeed worked under the environment of combined water and organics.

For the challenge involving the competing amine group in BSA (item (2)), adequate excess of coupling reagents were used to minimize the competition. Free amine groups on BSA may compete with oligonucleotide amines for coupling to the available carboxyl groups on BSA. Such competition reduces the oligonucleotide:BSA conjugation ratio. For bioprinting applications, it is desired to achieve a relatively high oligonucleotide:BSA conjugation ratio as long as these oligonucleotides do not come off during washes, as higher ratios provide higher signal intensity. Probes for such applications generally have oligonucleotide:BSA conjugation ratios between 1 and 2.4. This seems to be quite low. Theoretically, from the number of free carboxyl groups (Asp=41, Glu=58) as compared to free amine (Lys=60) groups on the BSA, it appears that higher conjugation ratios are possible as many free carboxyl groups on BSA should be available for oligonucleotide amines even if most of the BSA amines pair with their inter- or intra-molecular carboxyl groups.

For the challenge concerning the possibility of protein denaturation due to high ammonia concentration (item (3)), since the BSA protein is only used as a "membrane binder" in the assay, some denaturation should have minimal effect on the hybridization assay readout.

Since conventional processes rely on an extra HPLC step to purify the uncoupled BSA and reactants, manufacturing of these probes tends to be time consuming and expensive. If the present invention method is used to produce BSA conjugated probes at comparable or better quality, such methods would reduce the cost and time and become a very attractive alternative. In order to further demonstrate these advantages, conjugated probes were generated according to the present invention and their effectiveness in hybridization was evaluated.

The following outline provides a preferred experimental procedure in accordance with the present invention:

1. Oligonucleotide design, synthesis and the covalent attachment of a C-12 amino linker;
2. BSA activation and conjugation to the amino linker attached oligonucleotide;
3. Protein and DNA assays to determine the conjugation ratio; and
4. Hybridization assay.

1. Oligonucleotide Design, Synthesis and Covalent Attachment of a C-12 Amino Linker The oligonucleotide used was 5'-CAGACTTACGCAGCTCC-3', MW=5115.33 (SEQ ID NO: 1). This is a 17-mer containing identical complementary sequences to a PCR amplified product generated from a control DNA and a pair of primers in a primer mixture. Both of the control DNA and primers are supplied in a commercial genotyping kit (available from Dynal Biotech, CYnalRELI SSO strip Detection Reagent Kit, Cat No.: 802.01). This kit is used in the hybridization assay. The C-12NH linker provides a 12-carbon chain "spacer" between the amine group and oligonucleotide.

1. Four 0.2 umole columns were synthesized and C12-NH linkers (5'-Amino-Modifier C12 (C41H60N3O3P), Glen Research, Sterling, Va., Catalog Number: 10-1912-xx, MW: 673.92, F.W.: 263.32) were attached on the 5' hydroxyl groups (performed at Stanford University Protein And Nucleic Acids Facility on an Applied Biosystems DNA Synthesizer, Foster City, Calif.). The 5'-end amine was protected by MMT and all other protecting groups remained on the oligonucleotide (un-deprotected). The collection was stored at room temperature.
2. Obtain prepared oligonucleotide attached to support media by dislodging the column, drying the oligonucleotide-beads with house air and collecting the product on weighing paper. Divide into 5 parts of equal weights: two parts for the two conjugations, one part for analysis of MMT removal, and stored the rest for repeat experiments.

2. BSA Activation and Conjugation to the Amino Linker Attached Oligonucleotide

Reagents:
Bovine serum albumin, MW=66 kDa, Sigma-Aldrich (A-7906, St. Louis, Mo.) 1.0M HOBT/NMP (400662, Perkin Elmer, Wellesley, Mass.)
DIPEA/NMP (400136, Applied Biosystems)
PyBOP (100 mg/ml freshly dissolved in NMP before each use) (01-62-0016, Calbiochem-Novabiochem, San Diego, Calif.)–4° C.

Two different BSA concentrations were used in the experiments:
Exp. 1: Dissolve 0.8 mg BSA in 8 ul water
Exp. 2: Dissolve 1.6 mg BSA in 8 ul water
Both samples were then processed at room temperature in the following manner:
Mix with BSA activation solution:
Add 400 ul DMF
Add 2.7 ul of HOBT/NMP
Add 3.4 ul of DIPEA/NMP
Add 1.5 ul of PyBOP (100 mg/ml in NMP)

The BSA was mixed with activation solution for 30 seconds and then delivered into the oligonucleotide columns with a polypropylene syringe. The reaction solution was administered into the oligonucleotide columns and while the other side of the column was sealed with another syringe. The columns were rotated overnight at room temperature to achieve adequate mixing.

After overnight conjugation, a syringe was used to wash the columns with 3 ml of DMF twice. A fresh 20% (v/v) pipridine in DMF solution was prepared. 500 ul of this solution was administered into the column and incubated for 30 minutes.

The columns were washed again with 3 ml of DMF twice followed by 3 washes of 3 ml acetonitrile.

The sample was then dried with house air and the CPG-Oligo-NH-BSA was collected into a tube.

Next, 200 ul of 30% ammonium hydroxide was added. The mixture was then incubated at 55° C. for 5 hours to de-protect and cleave the oligo-NH-BSA off the CPG. The ammonia hydroxide was dried and the products were re-dissolved in 400 ul of purified water. A sample of 2 ul was taken, mixed with matrix and deposited on the Mass Spectrometer array to determine the molecular weights.

Mass Spectrometer Analysis
Molecular weights expected from Mass Spectrometer:

Oligo-C12-NH=5115.33+263.32=5378.65

Oligo-C12-NH-BSA=5378.65+66,000=71,378

Mass spectrometer results showed two peaks: one of the peaks was slightly less than 6 kDa and the other peak was at around 72 kDa. This indicated unconjugated oligonucleotide and conjugated oligonucleotide-BSA coexist in the products. Although mass spectrometry is not routinely used for quantitative purposes in this manner, in this case the large 72 kDa peak as compared to the tiny 6 kDa peak qualitatively suggested most of the oligos were conjugated to the BSA.

3. Protein and DNA Assays to Determine the Conjugation Ratio

In order to quantify the oligonucleotide:BSA conjugation ratio, the concentrations of BSA and oligonucleotide of the conjugate mixture were determined separately. BSA concentration was measured with a commercial protein BCA assay kit (Cat. No. 23227, Pierce Chemicals, Rockford, Ill.) while oligonucleotide concentration was calculated with a spectrophotometer reading at UV 260.

Protein Micro BCA Assay

The protein BCA (bicinchoninic acid) assay kit uses a well-known chemistry of reduction of $CU^{+2}$ to $Cu^{+1}$ by protein in an alkaline medium (the biuret reaction) with the highly sensitive and selective colorimetric detection of cuprous cation ($Cu^{+1}$) using a reagent containing bicinchoninic acid.

Since BSA was "activated" for conjugation to oligonucleotide, its reactivity for the BCA reagent should be confirmed in order to use this assay method. This was done by comparing BCA assays of BSA with and without activation.

Two identical sets of BSA, each set consisting of two vials of BSA (0.25 mg and 0.5 mg), were prepared for activation. Into the first set, stoichiometric amounts (as those used in conjugation activation step) of activators were added. In the second set (control), water replaced the activators. Both sets underwent the regular activation procedure. At the end of activation, samples withdrawn from the two sets were purified with a Compat-Able Protein Assay Preparation Reagent Set (Pierce Cat. No. 23215) to remove the activators which interfere with the BCA assay. The purified samples were then analyzed with BCA assays to determine their BSA concentrations.

The two sets of samples yielded identical concentration measurements, suggesting the activation process did not alter BSA reactivity for the BCA assay. They also yielded the same concentration measurements as a third and identical preparation of BSA that did not receive the activation procedure.

Since the conjugated samples contain oligo in addition to BSA, it is also necessary to know whether oligo contributed to the 562 nm absorbance in the BCA assay. From the absorbance of a control solution having an oligonucleotide concentration identical to the conjugation condition (ca. 0.16 umole in 400 ul water), it was determined that the absorbance of oligonucleotides at 562 nm is negligible.

With the BCA assay, the BSA concentrations in the two conjugates were determined to be 440 and 1,470 ug/ml. Divided by BSA molecular weight of 66,000 results in 6.67 and 22.27 umole/L for the two experimental samples started with 0.8 mg and 1.6 mg BSA, respectively.

$[BSA]_1$(for sample with 0.8 mg starting BSA)=6.67 umole/L (A-1)

$[BSA]_2$(for sample with 1.6 mg starting BSA)=22.27 umole/L(A-2)

OD260 Measurement for Oligonucleotide Concentration

Measurement of UV absorbance at 260 nm is the standard method to determine concentration of nucleic acids. However, in the presence of BSA in the mixture, it was again necessary to compensate for, if any, the absorbance by BSA. First of all, an absorbance curve of BSA at 260 nm was established by measuring a series of dilutions of BSA above and below the concentrations used in the conjugation experiments.

Y[BSA, ug/ml]=1793.5X (X=OD260 absorbance) with $R^2$=0.9898.

This is a very linear correlation and it shows BSA absorbance is negligible in its concentration range used for conjugation. Thus it is hypothesized that absorbance of 260 nm by oligonucleotide in the presence of BSA at conjugation concentrations would be approximately linear.

To prove the hypothesis, various amounts of oligonucleotides were mixed with BSA at two BSA concentrations (440 ug/ml & 1470 ug/ml, as determined above for the two conjugates) and their OD260 were taken.

As expected, OD260 correlated linearly with oligonucleotide concentrations from 4-fold below to 4-fold above the concentration (estimated) of the conjugates (ca. 0.16 umole in 400 ul water).

After least-square fitting of the measured data points within the range, we obtained:

For [BSA]=440 ug/ml, OD 260 curve is:

y [oligo, ug/ml]=28.666x (x=OD260), with $R^2$=0.9976

For [BSA]=1470 ug/ml , OD260 curve is:

y [oligo, ug/ml]=28.460x (x=OD260), with $R^2$=0.9986

Using the measured OD260 absorbance of the two conjugated samples in the above two equations, we obtained the oligonucleotide concentrations as 1320 ug/ml and 1460 ug/ml. These values were then divided by oligo molecular weight of 5115.33 to result in 258.05 and 285.42 umole/L.

$[oligo]_1$(for sample with 0.8 mg starting BSA)=258.05 umole(B-1)

$[oligo]_2$(for sample with 1.6 mg starting BSA)=285.42 umole(B-2)

Dividing (B-1) by (A-1) and (B-2) by (A-2), we obtained the oligonucleotide:BSA conjugation ratios as 38.69 and 12.82 for the two samples started with 0.8 mg and 1.6 mg BSA, respectively. This is reasonable, as higher amounts of starting BSA will likely result in lower effective oligonucleotide/BSA ratios. Excess BSA could have forced the reaction to equilibrate at higher intra- and inter-BSA molecular conjugations. However, the relatively high conjugation ratios are very desirable as signal intensity in DNA array applications is increased.

4. Hybridization Assay

The conjugated oligonucleotide-BSA was used in a hybridization reaction to determine its effectiveness for base pairing. The oligonucleotide used in this demonstration had a base sequence identical to one of the probes used in the Dynal Botech's SSO DRB1 tissue typing system and thus can be assayed with this kit. The conjugated oligonucleotide-BSA was diluted to a concentration equivalent to 100 ug/ml oligonucleotide and then 1 drop of 1 ul each of the two diluted samples were deposited on a DRB1 typing strip in a blank area next to pre-striped probes. The strip was left air-dry for an hour before assay. Control DNA amplification and hybridization followed the manufacturer's protocol. Both probes yielded blue color after hybridization and appeared brighter than their pre-striped counterpart probe on the strip. This indicates probes fabricated by this new conjugation process have retained functionality for hybridization.

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

I claim:

1. A process for producing an oligonucleotide-protein conjugate, said process comprising:
   providing a support media adapted for retaining an oligonucleotide;
   attaching an oligonucleotide to said support media;
   providing an albumin protein for subsequent coupling to said oligonucleotide; and
   coupling said protein to said oligonucleotide while said oligonucleotide is attached to said support media, to form a conjugate formed by said oligonucleotide and said protein removing said oligonucleotide-protein conjugate from said support media.

2. The process of claim 1 further comprising a step of:
   removing unconjugated protein from said support media.

3. The process of claim 1 wherein said albumin protein is bovine serum albumin (BSA).

4. The process of claim 1 wherein said support media includes glass beads.

5. A process for preparing protein conjugated oligonucleotides, said process comprising:
   providing a support media adapted for coupling an oligonucleotide;
   providing a first solution including said oligonucleotide;
   passing said first solution through said support media thereby coupling said oligonucleotide to said support media;
   providing a second solution including an albumin protein adapted to form a conjugate with said oligonucleotide;
   passing said second solution through said support media, after said passing of said first solution through said support media, thereby conjugating said protein with said oligonucleotlde while said oligonucleotide is coupled to said support media to form a conjugate formed by said oligonucleotide and said protein; and
   removing said protein conjugated oligonucleotides from said support media.

6. The process of claim 5 further comprising a step of;
   collecting said protein conjugated oligonucleotides.

7. The process of claim 5 wherein said protein is bovine serum albumin (BSA).

8. The process of claim 5 wherein said support media is selected from the group consisting of (i) controlled pore glass (CPG), (ii) oxalyl-controlled pore glass, (iii) copolymer of polystyrene/divinylbenzene, and (iv) poly(ethylene glycol) having a molecular weight between 5 kDa and 20 kDa.

9. The process of claim 5 wherein said step of providing said second solution is performed by:
   providing bovine serum albumin (BSA) as said albumin protein;
   dissolving said bovine serum albumin in water; and
   solubilizing said bovine serum albumin in an organic conjugation buffer.

10. A process for producing a conjugate of BSA end oligonucleotide, said process comprising:
    providing a support media adapted for coupling an oligonucleotide;
    passing an oligonucleotide through said support media and thereby coupling at least a portion of said oligonucleotide on said support media;
    after passing through and coupling said oligonucleotide to said support media, passing an effective amount of bovine serum albumin (BSA) through said support media and thereby forming said conjugate of BSA and oligonucleotide that is coupled to said support media;
    de-coupling said conjugate of BSA and oligonucleotide from said support media.

11. The process of claim 10 further comprising a step of:
    removing said conjugate of BSA and oligonucleotide from said support media.

12. The process of claim 10 further comprising:
    collecting said conjugate of BSA and oligonucleotide.

13. The process of claim 10 wherein said step of passing an effective amount of said BSA through said support media includes a step of attaching said BSA to said oligonucleotide.

* * * * *